US009017270B2

(12) United States Patent
Fausett et al.

(10) Patent No.: US 9,017,270 B2
(45) Date of Patent: Apr. 28, 2015

(54) APPARATUS AND METHOD OF DETECTING MOVEMENT OF OBJECTS WITHIN THE ABDOMINAL AND/OR PELVIC REGION

(75) Inventors: M. Bardett Fausett, San Antonio, TX (US); Jonathan W. Hander, Wappingers Falls, NY (US); Edwin W. Hander, Columbia, MO (US)

(73) Assignee: OB Technologies, LLC, San Antonio, TX (US)

( * ) Notice: Subject to any disclaimer, the term of this patent is extended or adjusted under 35 U.S.C. 154(b) by 376 days.

(21) Appl. No.: 13/052,649

(22) Filed: Mar. 21, 2011

(65) Prior Publication Data

US 2012/0245490 A1 Sep. 27, 2012

(51) Int. Cl.
*A61B 5/103* (2006.01)
*A61B 5/117* (2006.01)
*G01B 5/00* (2006.01)
*A61B 5/11* (2006.01)
*A61B 5/00* (2006.01)
*G01B 7/00* (2006.01)

(52) U.S. Cl.
CPC ... *G01B 5/00* (2013.01); *A61B 5/11* (2013.01); *A61B 5/4362* (2013.01); *G01B 7/003* (2013.01); *A61B 5/6851* (2013.01); *A61B 5/1114* (2013.01); *A61B 5/486* (2013.01)

(58) Field of Classification Search
USPC ............................ 600/304, 587–588, 591, 595
See application file for complete search history.

(56) References Cited

U.S. PATENT DOCUMENTS

| | | | | |
|---|---|---|---|---|
| 5,501,228 A * | 3/1996 | Lafontaine et al. | ........... | 600/505 |
| 5,551,424 A | 9/1996 | Morrison et al. | | |
| 5,566,680 A | 10/1996 | Urion et al. | | |
| 5,578,043 A * | 11/1996 | Galstian | ........................ | 606/119 |
| 5,911,694 A * | 6/1999 | Ikeda et al. | .................... | 600/587 |
| 5,951,497 A * | 9/1999 | Wallace et al. | ................ | 600/587 |
| 6,039,701 A * | 3/2000 | Sliwa et al. | ................... | 600/588 |
| 6,063,046 A * | 5/2000 | Allum | ........................... | 600/595 |
| 2003/0055360 A1* | 3/2003 | Zeleznik et al. | .............. | 600/587 |
| 2004/0242968 A1* | 12/2004 | Hill et al. | ....................... | 600/210 |
| 2008/0167553 A1* | 7/2008 | Paltieli et al. | ................. | 600/437 |
| 2009/0012432 A1* | 1/2009 | Sharf | ............................ | 600/588 |
| 2009/0192412 A1* | 7/2009 | Sela et al. | ..................... | 600/585 |
| 2010/0185122 A1 | 7/2010 | Fausett | | |

* cited by examiner

*Primary Examiner* — Rene Towa
(74) *Attorney, Agent, or Firm* — Arent Fox LLP

(57) ABSTRACT

Aspects of an apparatus and method for detecting movement of an object includes a base and a projection member extending between a first second ends, wherein the first end is attached to the base. Further included is a support member at the second end of the projection member, and a guide wire carried by the support member and having a substantially fixed length, wherein the guide wire is movable between a first position and a second position in conjunction with movement of an object. Also included is a sensor located a substantially fixed distance along a path of the guide wire from the support member, wherein the sensor detects movement of the guide wire between the first second positions. Additionally included is a feedback unit in communication with the sensor, wherein the feedback unit is configured to generate feedback corresponding to the detected movement.

21 Claims, 12 Drawing Sheets

APPARATUS AND METHOD OF DETECTING MOVEMENT OF OBJECTS WITHIN THE ABDOMINAL AND/OR PELVIC REGION

BACKGROUND

The described aspects relate to detecting movement of objects, such as objects within the abdominal and/or pelvic region of a body. For example, in one aspect, the described apparatus and methods relate to childbirth, and particularly to apparatus and methods of measuring fetal station and descent in real time.

Regional anesthesia, including epidurals, is commonly used during labor. Childbirth under regional anesthesia inhibits the natural physiologic feedback from the nervous system that promotes effective maternal expulsive efforts. Because of the lack of natural sensory feedback, mothers—especially those who are experiencing childbirth for the first time—lack the natural sensation, inherent urge and ability to generate effective pushing. This prolongs labor resulting in increased maternal, fetal, and neonatal morbidity and an increased time burden on the delivery staff and facilities.

With additional coaching from knowledgeable delivery attendants, the mother can be provided with extra-biological feedback improving her ability to successfully move the baby through the birth canal. The most effective coaching involves the ability to provide the mother immediate feedback and guidance in response to her expulsive efforts. This typically requires frequent or even constant digital, e.g. with a human finger, vaginal examination to evaluate fetal position and descent. However, these vaginal examinations increase the risk of maternal and fetal infection and tissue trauma. In addition to the health risks of coaching using vaginal examination, such a process requires the direct time and attention of professional attendants. This adds to the time-burden of the delivery-room staff.

Thus, improvements in monitoring the movement of objects within the abdominal and/or pelvis region are desired.

BRIEF SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In accordance with one aspect of the present invention, a device is used to monitor the fetal descent and velocity of the baby with respect to a fixed position during labor. The data from this device are then processed and used to provide real-time feedback to the mother, enabling her to push more effectively. For example, the feedback provides a mother with a measure of the effectiveness of her expulsive efforts, e.g. during the second stage of labor, which in an aspect allows her to learn more quickly how to be maximally effective, and which further provides motivation for the mother. In an additional aspect, the feedback may also be associated with a goal for the mother to achieve during each contraction to further increase efficacy and shorten the second stage of labor.

In an aspect, the described apparatus and methods may provide immediate feedback to the mother, without requiring digital vaginal examinations, which allows timely intervention and maximizes the effectiveness of maternal expulsive efforts. In an aspect, the feedback may be provided to the mother in a simple enough way to be comprehended even under the duress of labor. Since mothers oftentimes have their eyes closed during pushing, optionally or in addition to visual feedback, audible and/or tactile feedback may be provided to allow constant feedback regardless of the mother's visual attention to a monitor displaying the visual feedback.

In an additional aspect, the feedback can also be used as a motivational tool to help increase a mother's pushing efficacy. For example, the feedback may be in the form of a gauge having a target level of movement for a pushing event. The target level can be set manually by the delivery staff or be automatically set based on prior performance. In order to further engage the mother's attention, in an aspect, the feedback may be delivered in an interactive format such as a game where effective expulsion generates a positive response such as a higher score or a visually successful event such as a runner clearing a hurdle or the lack of a negative response such as a jumper failing to clear a barrier.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

The present aspects will be more fully understood in light of the following detailed description taken together with the accompanying drawings.

BRIEF DESCRIPTION OF THE DRAWINGS

For a more complete understanding of the present aspects, reference is now made to the following descriptions taken in conjunction with the accompanying drawing in which.

DETAILED DESCRIPTION

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Figure 1:
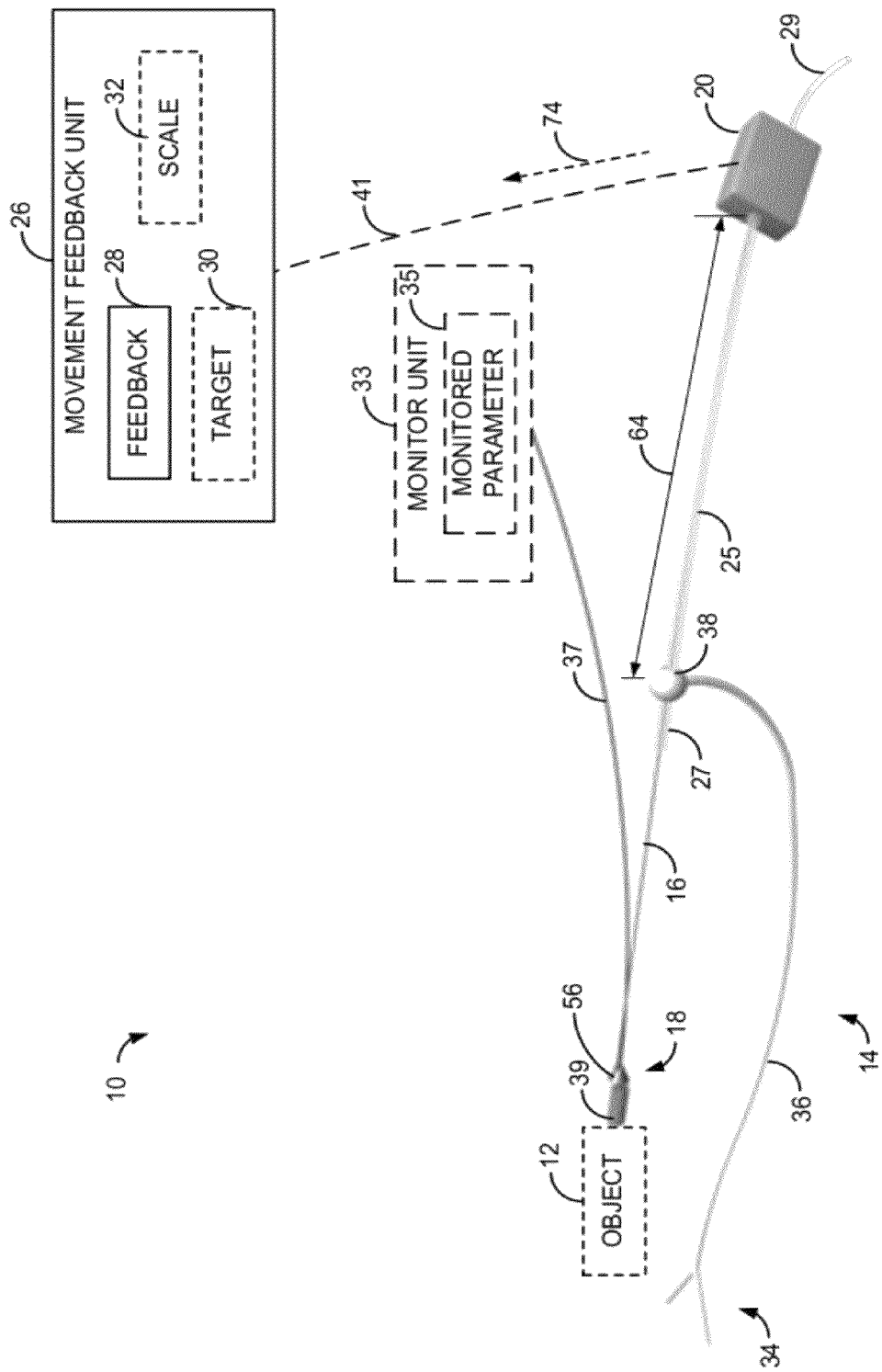
FIG. 1 is a perspective view from a first side of an aspect of an apparatus for detecting and/or measuring movement of objects, such as objects within the abdominal and/or pelvic region of a body.
Figure 2:
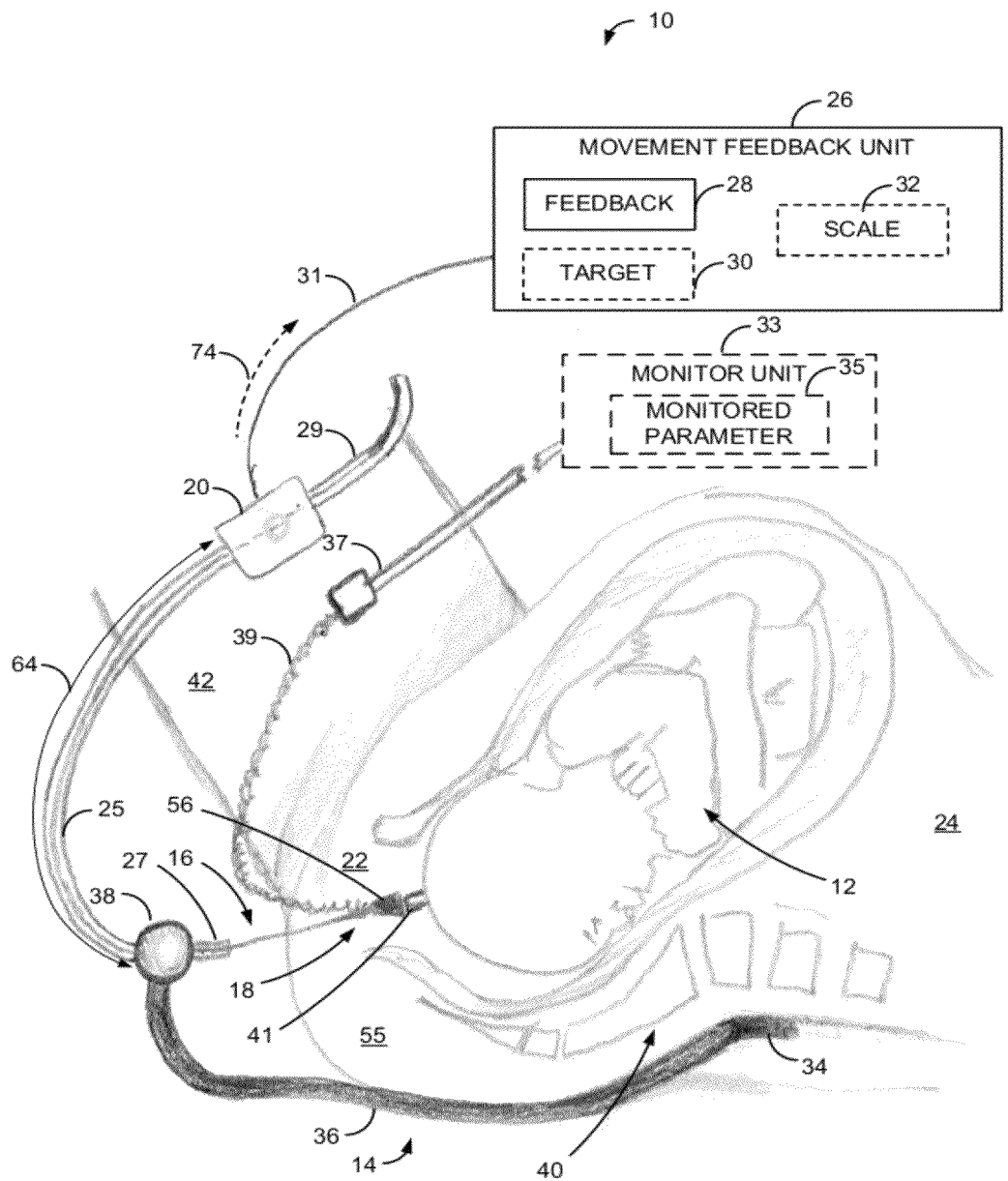
FIG. 2 is a perspective view from a second side opposite the first side of FIG. 1 of the apparatus for detecting and/or measuring movement of objects, including the apparatus positioned for measuring fetal descent.
Figure 3:
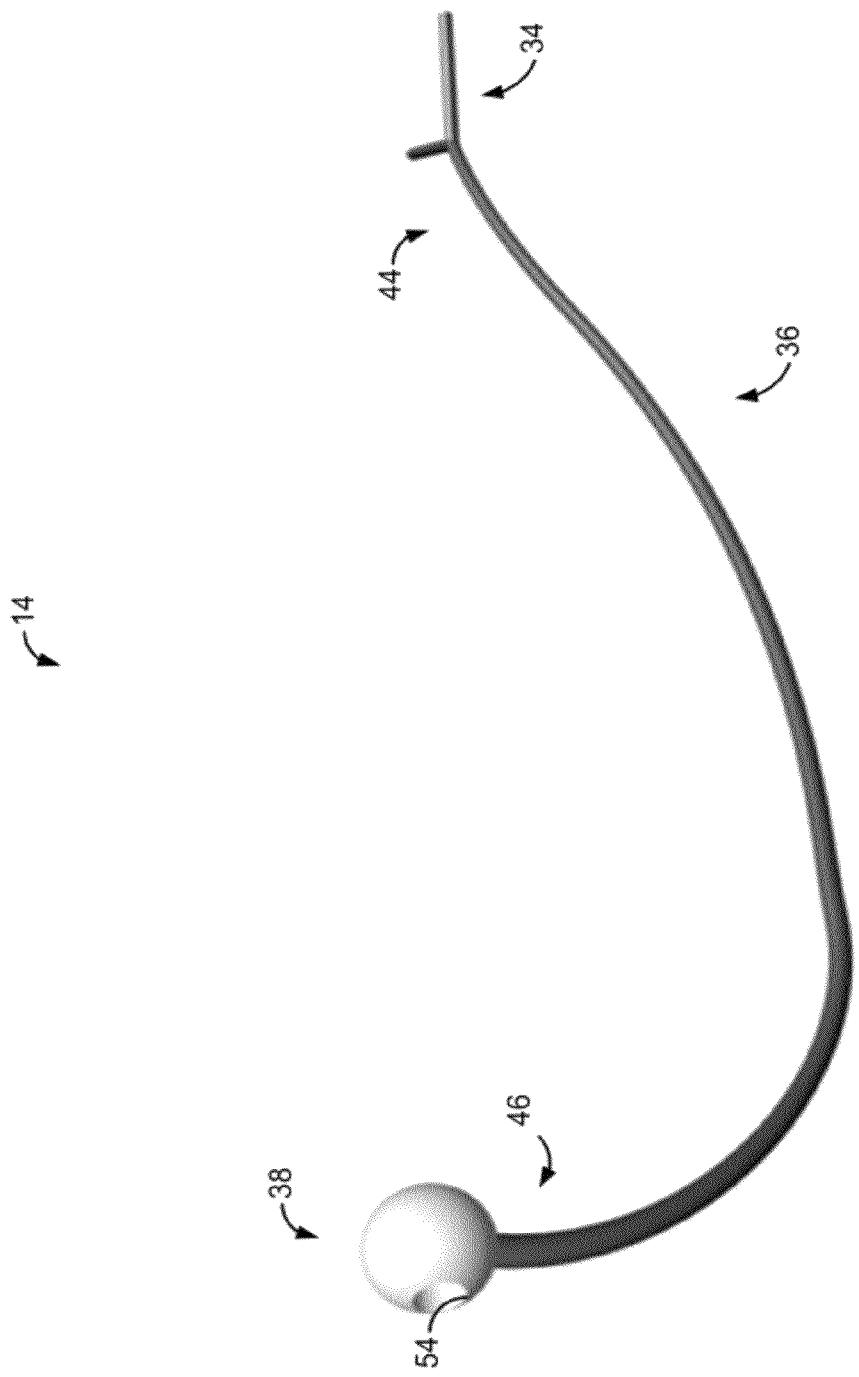
FIG. 3 is a perspective view of an aspect of a mount of the apparatus of FIG. 1.
Figure 13:
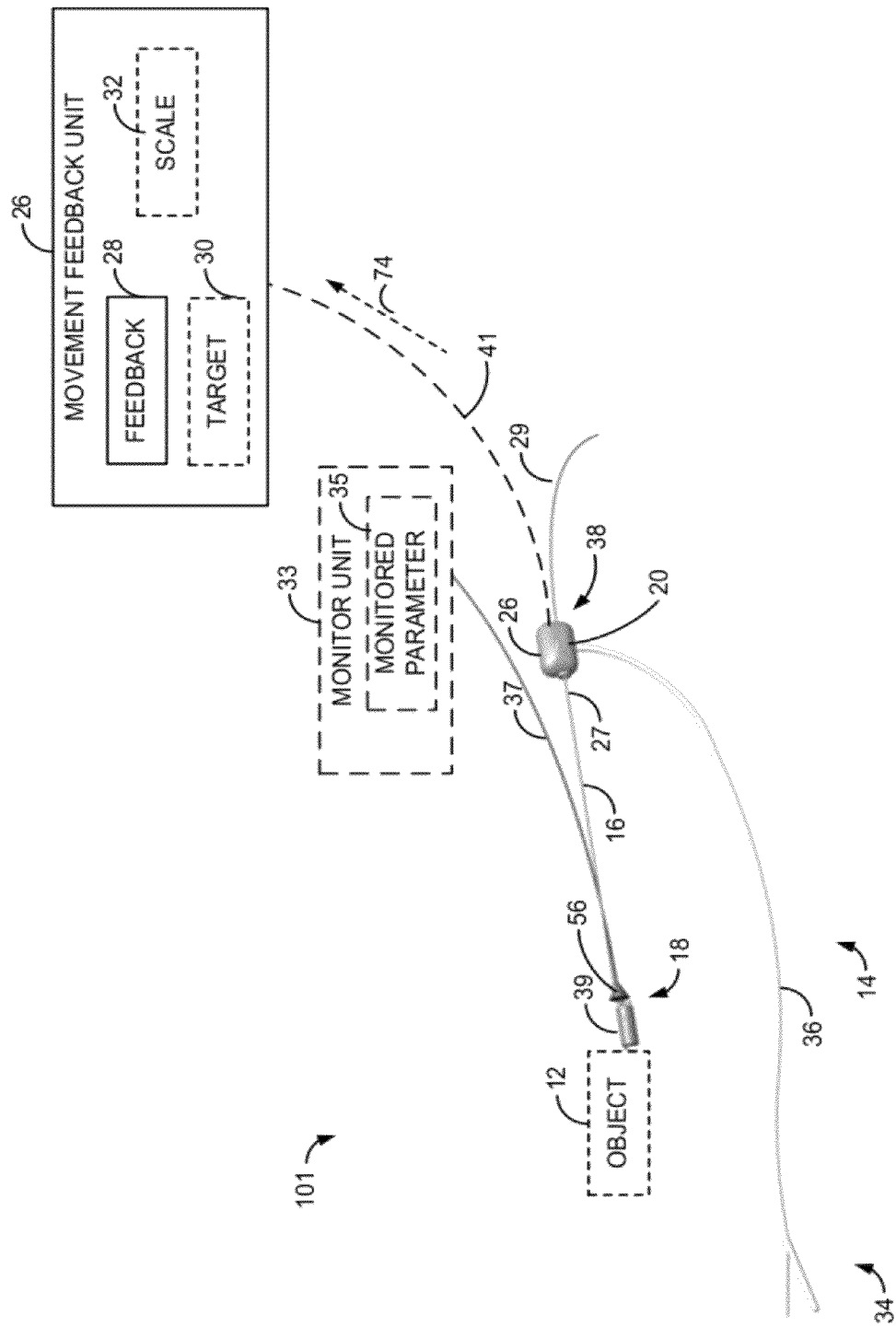
FIG. 13 is a perspective view of an apparatus similar to the apparatus of FIG. 1.

Referring to FIGS. 1, 2 and 13, in one aspect, an apparatus 10 or 101 for detecting and/or measuring movement of an object 12 includes a mount 14 that movably supports a guide wire 16, which has a first end 18 attachable to object 12, and a sensor 20 that detects the movement of guide wire 16 corresponding to the movement of object 12. For example, referring specifically to FIG. 2, in an aspect, object 12 is located in abdominal/pelvic region 22 of a body 24, and thus movement of object 12 within body 24 may include but is not limited to movement of a fetus in a birth canal. Additionally, apparatus 10 or 101 may include a feedback unit 26 in communication with sensor 20. Feedback unit 26 is configured to generate feedback 28 corresponding to the movement detected by sensor 20 In an aspect, for example, feedback unit 26 receives a movement signal 30 and generates feedback 28 in relation to one or more of the characteristics of the detected movement represented by movement signal 30.

For instance, feedback 28 may be one or any combination of audio feedback, visual feedback, or tactile feedback. Further, for example, feedback 28 may be a metric corresponding to the detected or measured movement, or feedback 28 may be a reward corresponding to the detected or measured movement, or both. For instance, feedback 28 including a metric may be a magnitude, a velocity or an acceleration of the movement. Also, for instance, feedback 28 including a reward may be some audio, visual and/or tactile output that is one or more of interesting, pleasing, desired, superfluous, etc. in order to reward someone, e.g. a mother, for efforts in producing the movement. In an aspect relating to detecting and/or measuring fetal position, for example, feedback 28 may provide a mother, as well as a doctor or other hospital staff, with information on an instantaneous (e.g. associated with a single push) and/or a cumulative result (e.g. associated from some starting point of the labor) of her efforts to push the fetus down the birth canal, including one or more of a magnitude, a velocity, or an acceleration.

Optionally, apparatus 10 or 101 may further include a guide tube 25 extending at least between an end of mount 14 and sensor 20. Guide tube 25 allows sensor 20 to be located remotely from mount 14, and provides further support for movements of guide wire 16. For example, in an aspect, sensor 20 may be affixed to a leg of a patient and mount 14 and/or support member 38 may be located adjacent to an abdominal or pelvic region of the patient, and guide tube 25 extends between sensor 20 and mount 14 and/or support member 38 and allows the patient to move their leg substantially without causing guide wire 16 to move relative to sensor 20 and mount 14 and/or support member 38. In a further optional aspect, an extending portion 27 of guide tube 25 may project from a portion of mount 14 toward object 12 in order to help transition guide wire 16 into a position to be supported by mount 14. In yet another optional aspect, another extending portion 29 of guide tube 25 may project from sensor 20 so that movements of guide wire 16 beyond sensor 20 are not interfered with and/or so that guide wire 16 does not poke objects in the vicinity of sensor 20.

Also optionally, as is discussed below in more detail, feedback unit 26 may present one or both of a target 30 or a scale 32 against which feedback 28 may be compared.

In a further option, apparatus 10 or 101 may include or may work in combination with a monitor unit 33 that outputs a monitored parameter 35, such as a heartbeat of a fetus. For example, in an aspect, monitor unit 33 may be connected via a communication link or signal transport mechanism 37, such as wires or a cable or a wireless technology, to a fetal scalp electrode 39, which thereby allows measurement and output of the heartbeat of the fetus.

Thus, apparatus 10 or 101 enables the detection and/or measurement of movement of object 12, such as a fetus or other biological member within abdominal/pelvic region 22 of body 24, and the output of such movement as feedback 28 presented by feedback unit 26. For example, in an aspect relating to detecting and/or measuring fetal position, apparatus 10 or 101 may be a metrology device to measure and provide feedback on fetal position with respect to a starting point during a second stage of labor, and, optionally, to measure and provide feedback on velocity of the movement during pushing events.

Referring to FIGS. 1-4, in an aspect, mount 14 includes a base 34, a projection member 36 extending from base 20, and a support member 38 at the distal end of projection member 36 for movably supporting guide wire 16. Alternatively, referring to apparatus 101 of FIG. 13, mount 14 may not include support member 38, but instead mount 14 may attach to sensor 20, which includes or defined support member 38. In another alternative, such as in FIG. 13, mount 14 may include sensor 20, which further includes or defines support member 38. It should be noted that base 34, projection member 36 and support member 38 may be an integral unit or separate components. In an aspect, for example relating to detecting and/or measuring fetal descent, projection member 36 is movably positionable relative to base 34 so that support member 38 can be located at a suitable position outside of the birth canal to receive guide wire 16 and allow guide wire 16 to move relative to support member 38 substantially without resistance in correspondence to movement of object 12, e.g. fetus in this case. Additionally, base 34 is positionable in a substantially fixed manner adjacent to a pelvic or sacral region 40 (FIG. 2) of body 24 so that movement of object 12 relative to pelvic or sacral region 40 can be distinguished from movement of object 12 relative to other objects or body portions outside of pelvic or sacral region 40. In other words, for example in an aspect relating to detecting and/or measuring fetal position, movement of object 12, e.g. a fetus, relative to pelvic or sacral region 40 can be isolated from movement of the fetus relative to, for example, a leg 42 (FIG. 2) or other body part that may move during childbirth.

For example, base 34 may be shaped to resist movement relative to pelvic or sacral region 40. For instance, base 34 may include a Y-shaped configuration, but other shapes may be possible, including solid shapes, e.g. a sold V-shaped or Y-shaped body as opposed to the illustrated Y-shaped extensions.

Projection member 36 may be a wire or tube that may be connected at a proximal end 44 to base 34 and bent into a desired shape to position support member 38. In other words, in an aspect, projection member 36 may be substantially inelastic such that projection member 36 may be bent and remain substantially in the bent position. For example, in one aspect that should not be construed as limiting, projection member 36 may be a wire having a gauge or thickness sufficient to provide mount 14 with a conformable configuration while resisting movement of mount 14 during movement of guide wire 16 relative to sensor 20.

Figure 4:
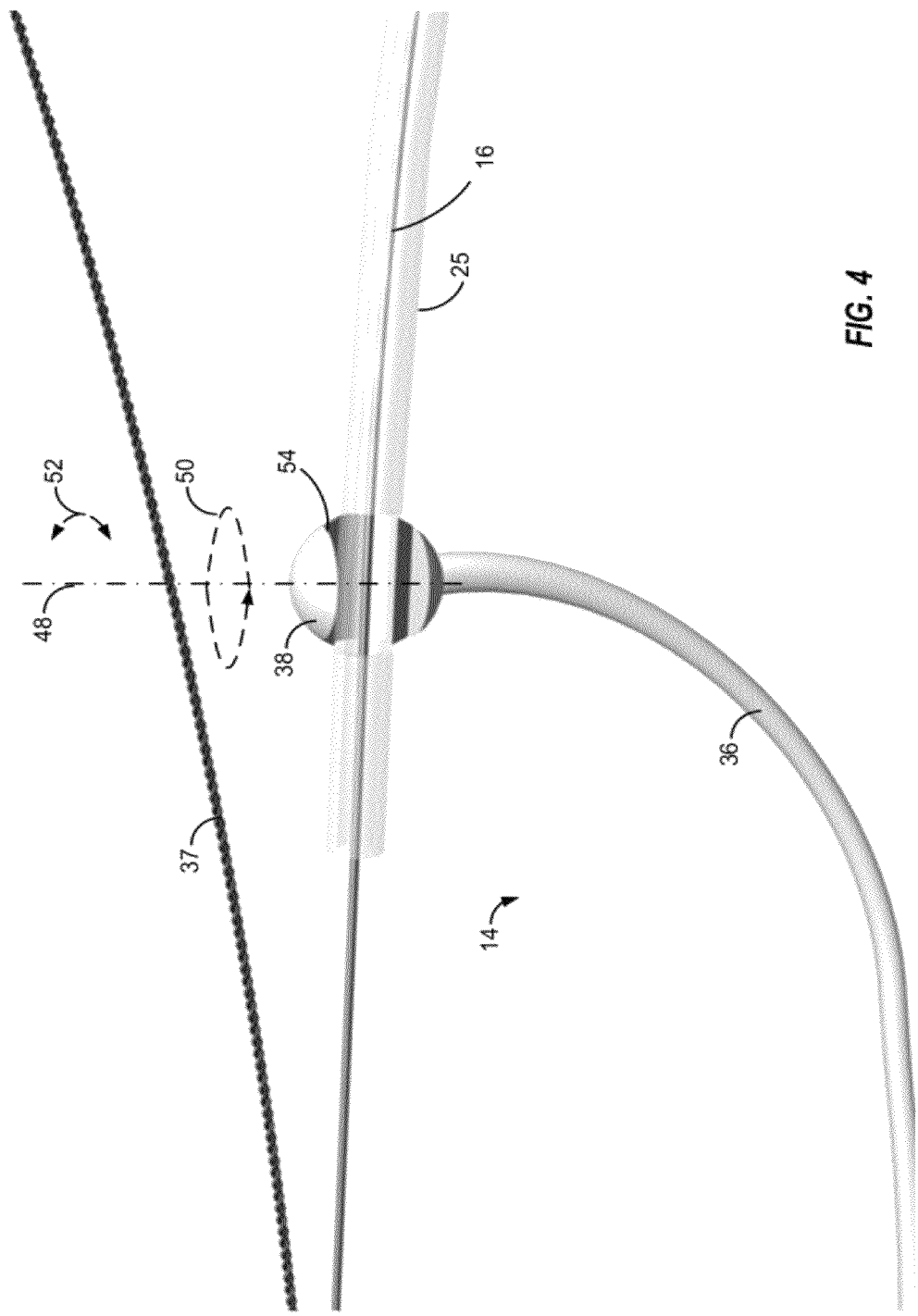
FIG. 4, is a close-up side view of a portion of the mount of FIG. 1, including a partial cross-sectional view of an aspect of a support member of the mount.
Figure 5:
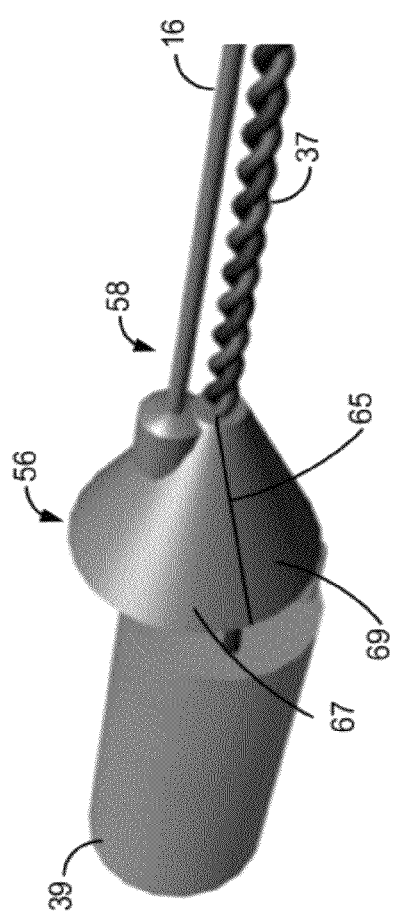
FIG. 5 is a perspective view of an aspect of a guide wire mount connecting the guide wire of the apparatus of FIG. 1 to a fetal scalp electrode.
Figure 6:
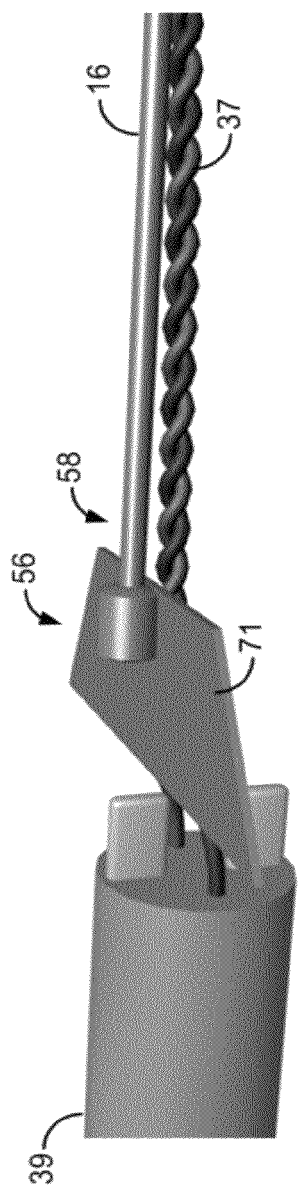
FIG. 6 is a perspective view of another aspect of a guide wire mount.

Support member 38 is integral with or connected to a distal end 46 of projection member 36. In an aspect, support member 38 is movably connected to projection member 36, for example, to accommodate or allow some degree of oblique movement of guide wire 16 relative to projection member 36. For example, support member 38 may be at least partially rotatable about or relative to an axis 48 of projection member 36, as illustrated in FIG. 4 by arrows 50 and 52. Further, for example referring to FIG. 4, in an aspect support member 38 may be a spherical member, either solid or hollow, having a through hole 54 for receiving guide wire 16. Optionally, in an aspect where support member 38 is hollow, through hole 54 may include two opposing circular surfaces defined by walls on opposite sides of the hollow sphere. In another optional aspect, through hole 54 may be sized to accommodate guide tube 25, which in some aspects may extend through support member 28 and project toward object 12, such as fetus. In an aspect, guide tube 25 is elastic, and as such the extending portion 27 of guide tube 25 helps to accommodate for misalignment between guide wire 16 and through hole 54 of support member 38 by providing a bending transition that directs guide wire 16 toward through hole 54. In a further aspect, support member 38 may be only through hole 54 through distal end 46 of projection member 36. Additionally, in an aspect, support member 38 may be positionable to a location having a substantially fixed distance to base 34, for example, to isolate movement of object 12 relative to pelvic or sacral region 40 to which base 34 is affixed as detected through the movement of guide wire 16 that is carried by support member 38.

In an aspect, referring to FIG. 2, mount 14 may be positioned against body 24 such that projection member 36 extends between the buttocks 55 and support member 38 is spaced away from body 16 to allow access to the vaginal area/birth canal, but to allow support member to receive and carry guide wire 16. For example, in an aspect, mount 14 may be affixed to body by tape or some other adhesive, straps, specially designed clothing, or any other mechanism for maintaining mount 14 is a fixed position relative to pelvic or sacral region 40. Further, in another aspect, mount 14 may be held in place adjacent to pelvic/sacral region 40 by the weight of body 24 against a support member, such as a surface of a mattress, bed, table or gurney.

Referring to FIGS. 1, 2, 5 and 6, guide wire 16 may be a wire that is substantially inelastic but having sufficient flexibility to extend from object 12 to support member 38 and from support member 38 to sensor 20, in some case along a curved path, without kinking or causing a change in length of wire along a path to sensor 20 that is not commensurate with an amount of movement of object 12. For example, in one aspect that should not be construed as limiting, guide wire 16 may be a wire having a sufficient gauge or thickness to resist expanding or contracting during movement of object 12 or during movement of guide wire 16 relative to sensor 20. For example, guide wire 16 may be a wire such as a vascular guide wire.

Further, in an aspect, a mount 56 may connect a proximal end 58 of guide wire 16 to object 12 or to a component 39, such as a fetal scalp electrode, connected to object 12. For example, mount 56 may attach to component 39 or to other members 37, such as wires, extending from component 39. For example, referring to FIG. 5, in an aspect, mount 56 may be a hollow, elastic member having a longitudinal slot 65 that defines opposing flanges 67 and 69 that may be temporarily deformed to allow mount 56 to clip onto members 37, such as wires. In another aspect, referring to FIG. 6, in an aspect, mount 56 may be a planar member 71 having an elastic memory that defines a cone shape, whereby the planar member can be opened up and wrapped about members 37, e.g. wires, based on the elastic memory of the material. It should be noted, however, that other attachment mechanisms may be utilized. Further, the attachment of mount 56 to component 39 or members 37 may be sufficiently strong so that mount 56 does not move relative to component 39 or members 37.

Figure 7:
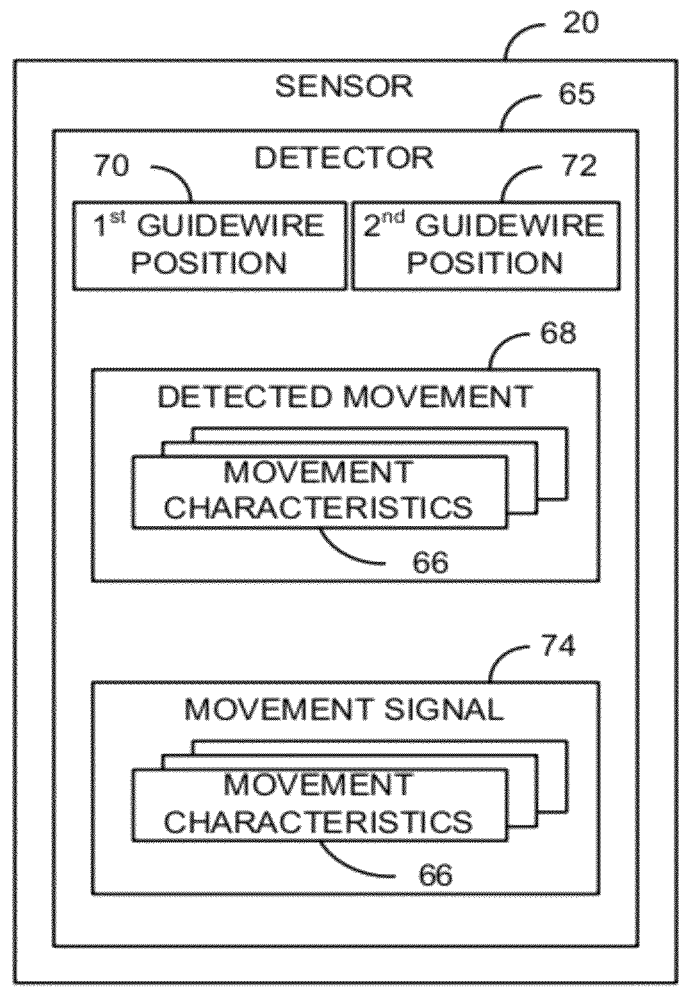
FIG. 7 is a schematic block diagram of an aspect of a sensor of the apparatus of FIG. 1.

Referring to FIGS. 1, 2 and 7, sensor 20 is positioned adjacent to a portion of guide wire 16 and located a substantially fixed path distance 64 along a guide wire path from mount 14. For example, fixed path distance 64 may have any value, including a zero value. For example, referring to FIG. 13, it is noted that fixed path distance 64 of a zero value may occur, for instance, when sensor 20 also includes support member 38. In other words, sensor 20 may be located remotely from mount 14 or on mount 14. In an aspect, sensor 20 includes a detector component 65 that identifies and/or measures movement of guide wire 16. Moreover, in an aspect, guide wire 16 may have a substantially fixed length, or may be substantially inelastic, and is thus movable between a first position and a second position in conjunction with movement of object 12. Accordingly, based at least on fixed path distance 64 and the inelasticity of guide wire 16, sensor 20 is configured to detect and/or measure one or more characteristics 66 of movement 68 of guide wire 16 between a first position 70 and a second position 72. In an aspect, guide wire 16 is movable in a sequence of movements between first position 70 and second position 72, wherein the sequence of movements correspond to a movement of the object relative to at least one of an abdominal region or a pelvic region of a body. For example, the sequence of movements may correspond to a fetal descent, or descent of a bladder or uterus. In an aspect, for example, sensor 20 generates a movement signal 74 representing the one or more characteristics 66 of detected movement 68. Signal 74 may be communicated to feedback unit 26, for example, via a communication link or signal transport mechanism 41, such as but not limited to a wire or cable, or a wireless technology, such as cellular or BLUETOOTH. In an aspect, for example, sensor 20 may be any type of sensor able to detect and/or measurement movement of guide wire 16, such as an optical sensor, an electrical sensor, a magnetic sensor, or a mechanical sensor such as a servo unit.

Figure 8:
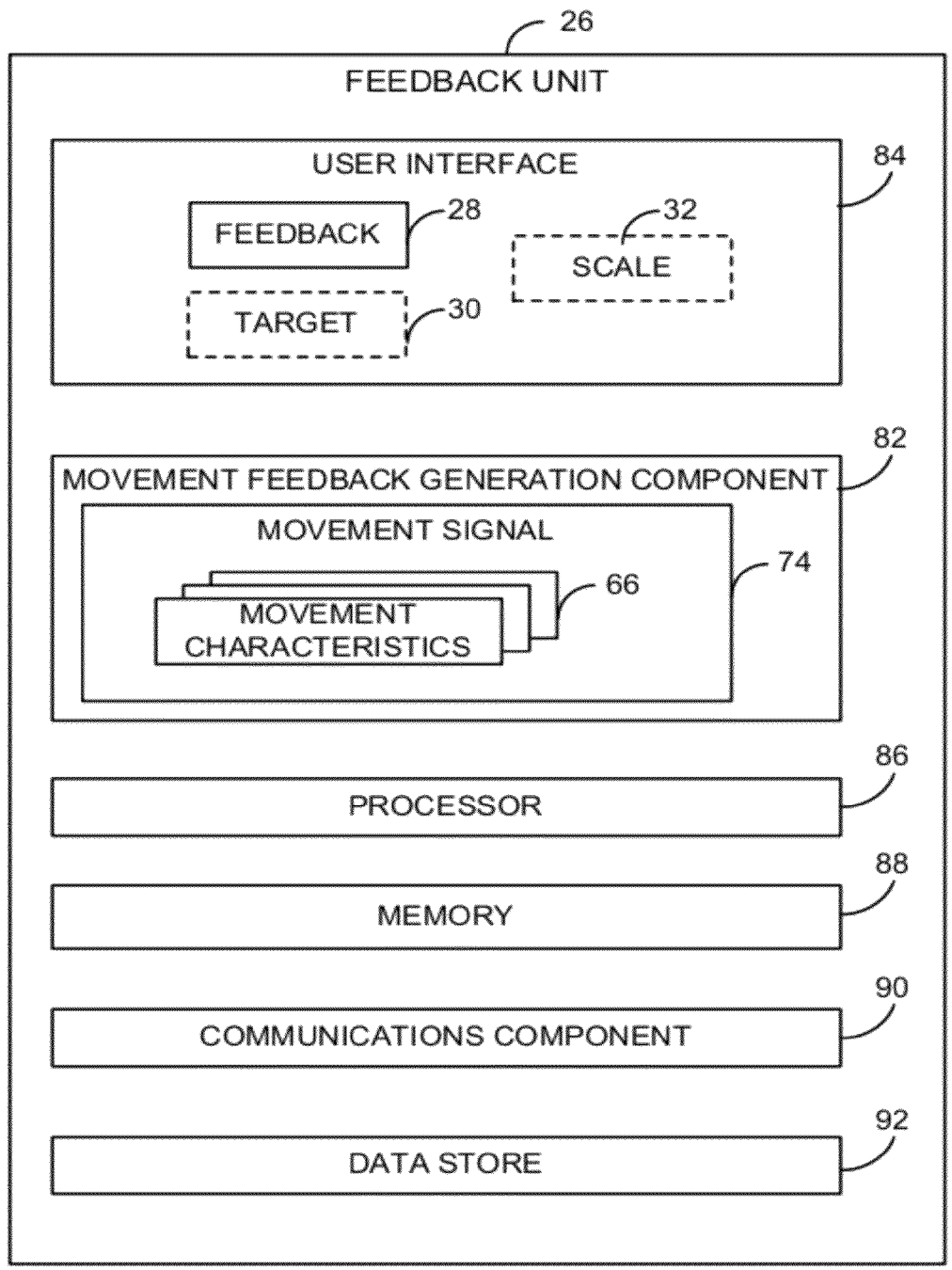
FIG. 8 is a schematic block diagram of an aspect of a feedback unit of the apparatus of FIG. 1.

Referring to FIGS. 1, 2 and 8, feedback unit 26 may be a computer device having a movement feedback generation component 82 that includes functions, algorithms or computer programs for receiving movement signal 74 and the one or more movement characteristics 66, and causing user interface 84 to output feedback 28.

In an aspect, for example, feedback unit 26 includes a processor 86 for carrying out processing functions associated with executing movement feedback generation component 82. Processor 86 can include a single or multiple set of processors or multi-core processors. Moreover, processor 86 can be implemented as an integrated processing system and/or a distributed processing system.

Feedback unit 26 further includes a memory 88, such as for storing local versions of applications being executed by processor 86, such as a program associated with movement feedback generation component 82. Memory 88 can include any type of memory usable by a computer, such as random access memory (RAM), read only memory (ROM), tapes, magnetic discs, optical discs, volatile memory, non-volatile memory, and any combination thereof.

Further, feedback unit 26 may include a communications component 90 that provides for establishing and maintaining communications with one or more other devices or components utilizing hardware, software, and services as described herein. Communications component 90 may carry communications between components on feedback unit 26, as well as between feedback unit 26 and external devices, such as devices located across a communications network and/or devices serially or locally connected to feedback unit 26, such as sensor 20. For example, communications component 90 may include one or more interfaces and/or buses, and may further include a transmitter and receiver, respectively, operable for interfacing over wirelines or wirelessly with external devices.

Additionally, feedback unit 26 may further include a data store 92, which can be any suitable combination of hardware and/or software, that provides for mass storage of information, databases, and programs employed in connection with aspects described herein. For example, data store 92 may be a data repository for applications not currently being executed by processor 86.

As noted above, feedback unit 26 may additionally include a user interface component 84 operable to receive inputs from a user of feedback unit 26, and further operable to generate outputs, such as feedback 28, targets 30 or a scale 32, for presentation to the user. User interface component 96 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, user interface component 96 may include one or more output devices, including but not limited to a display, a speaker, a haptic feedback mechanism, a printer, any other mechanism capable of presenting an output to a user, or any combination thereof.

In an aspect relating to detecting and/or measuring fetal position, for example, apparatus 10 may be a metrology device to measure second stage of labor fetal position with respect to a starting point, and, optionally, velocity during pushing events. In an aspect, the device includes mount 14 with an integrated support member 38, a disposable guide tube 25, and sensor 20. The sensor 20 may be an optical sensor that detects movement of guide wire 16, which may also be referred to as a bristle, as the bristle moves across a sensor window. In an aspect, one end of the bristle may mounted to a fetal scalp electrode (FSE) 39 affixed to the fetus, and thus movement measured by the metrology device directly corresponds to fetal descent. In an aspect, a window on the optical sensor 20 protects the optical components, allows for easy cleaning which enables reuse, but does not prevent accurate measurement of bristle movement. Support member 28 of mount 14 and guide tube 25 serve to guide the bristle 16 directly across the optical sensor 20, which is positioned at a constant distance from mount 14, or at least a constant distance along the path of bristle 16 from support member 28, thereby allowing stable measurement. In an aspect, guide tube 25, which may be a disposable part, may be made of a flexible material such as plastic tubing that can be shaped by the delivery staff after the metrology unit has been affixed to the mother to allow the guide wire or bristle 16 to travel in an unhindered manner as labor progresses.

In accordance with this aspect, a thin, flexible wire or 'bristle' 16 such as a vascular guide wire is mounted to the fetal end of a fetal scalp electrode (FSE) 39. The bristle mount 56 may be constructed of a semi-elastic material with a relaxed position in a conical formation. To apply the bristle 16 using the bristle mount 56 to a standard fetal scalp electrode 39, the mount 56 is uncoiled. Once uncoiled, mount 56 can be placed above the FSE 39 and around wires 37, and allowed to coil back to its relaxed position around the FSE 39 and/or wires 37. The bristle mount 56 can then be adjusted closer to the baby's head by sliding it along the twisted pair of wires 37. The conical nature of the bristle mount 56 minimizes slippage back up the twisted pair of wires 37. When the FSE 39 is affixed to the fetus 12, the bristle 16 extends outside of the vagina allowing attachment of the bristle/wire 16 through support member 28 and sensor 20. Mount 14 (see, e.g. FIG. 2) may be attached to body 24 with base 34 adjacent to pelvic or sacral region 40 using such material as sticky tape, soft stretchy belt material (e.g. fetal monitoring belts), or modified underclothing to the mothers upper thigh, lower stomach, perineum, vagina, anal area, sacral area, labial crural fold, or another biomedical device (e.g., a HEMAVERT perianal stabilizer instrument) or maternal bed or device attached thereto.

The metrology device 10 can function to detect the movement of the bristle/wire 16 extending from the fetus 12 using the optical sensor 20. Movement of the wire 16 over a detection area of sensor 20 is converted to the movement signal 74 that is conveyed to the feedback unit 26 where the signal 74 is converted into one or more of visual, auditory or tactile feedback 28. Proper fixation and positioning of the metrology device 10, e.g. to isolate movement of the fetus 12 relative to the mount 14, maximizes the signal to noise ratio. The noise generated by maternal positioning movement can also be distinguished from the fetal movement by other methods such as a dual wire fixed position comparator or accelerometer.

In this aspect, sensor 20 is connected to the feedback unit 26 using a cable 31 (FIGS. 1 and 2), and sensor 20 processes detected movement 68 and converts it to a movement signal 74. Movement signal 74 is then translated by the movement feedback generation component 82, which may be software, into the desired feedback 28. In an aspect, feedback unit 26 is situated such that the mother can see and/or hear and/or feel responses, e.g. feedback 28, signaling fetal movement in real time. For example, the feedback unit 26 may be located on or near the delivery bed of the mother, allowing her ready access to the feedback. The positioning allows visual, auditory and tactical feedback 28 reflecting fetal movement in real-time. In an aspect, the extent and velocity of fetal movement is portrayed to the mother as feedback 28 by feedback unit 26 in a manner relating to the effectiveness of uterine contractions and maternal expulsive effort (hereafter referred to as "push"). The feedback 28 is real time and interactive, facilitating rapid maternal motivation and learning. In an aspect, one or more targets 30 for fetal movement can be automatically generated based on previous efforts or manually adjusted by a birth attendant.

Figure 10:
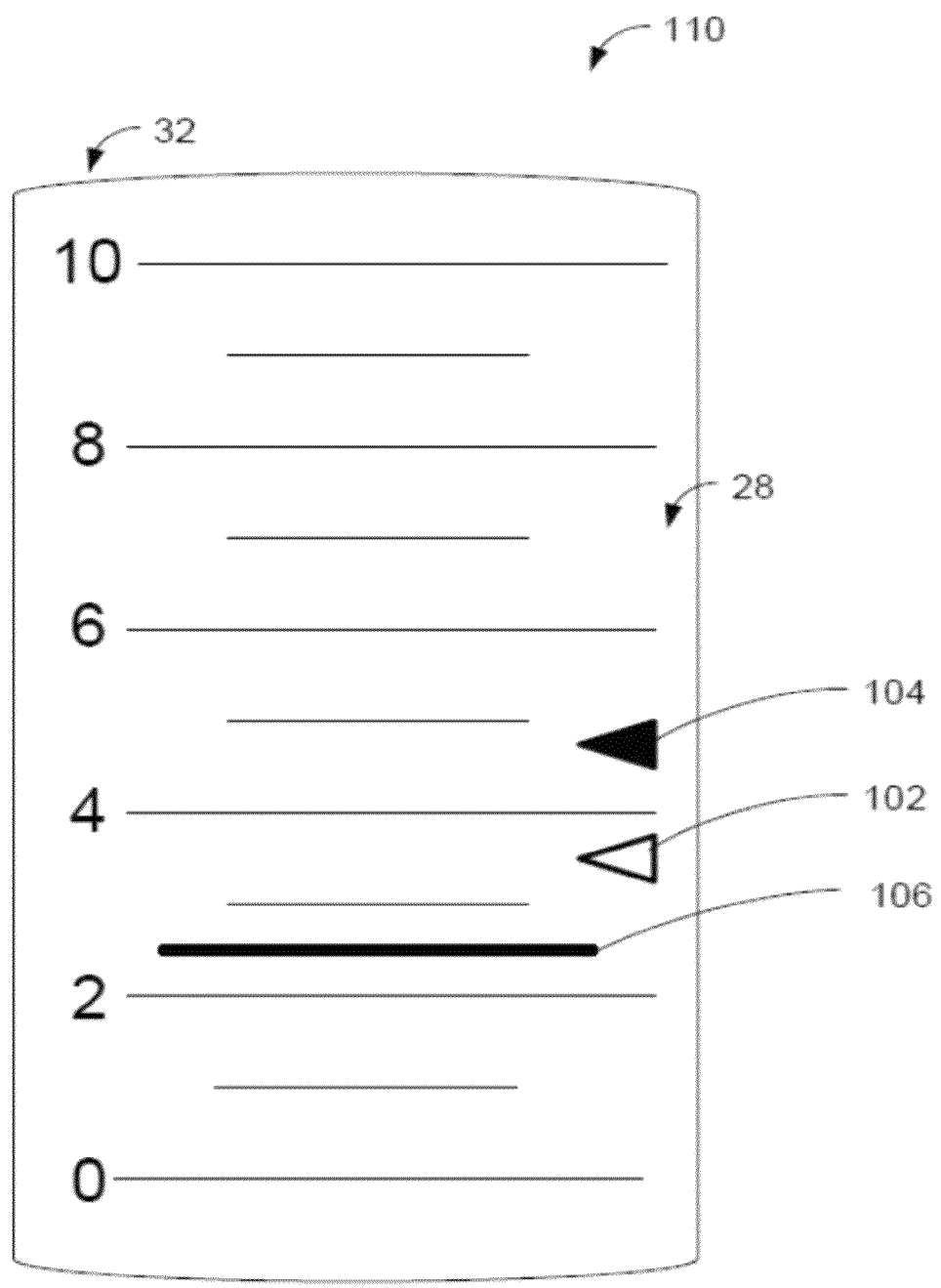
FIG. 10 is a front view of an aspect of an output or display of the feedback, e.g. in the form of a linear gauge.
Figure 11:
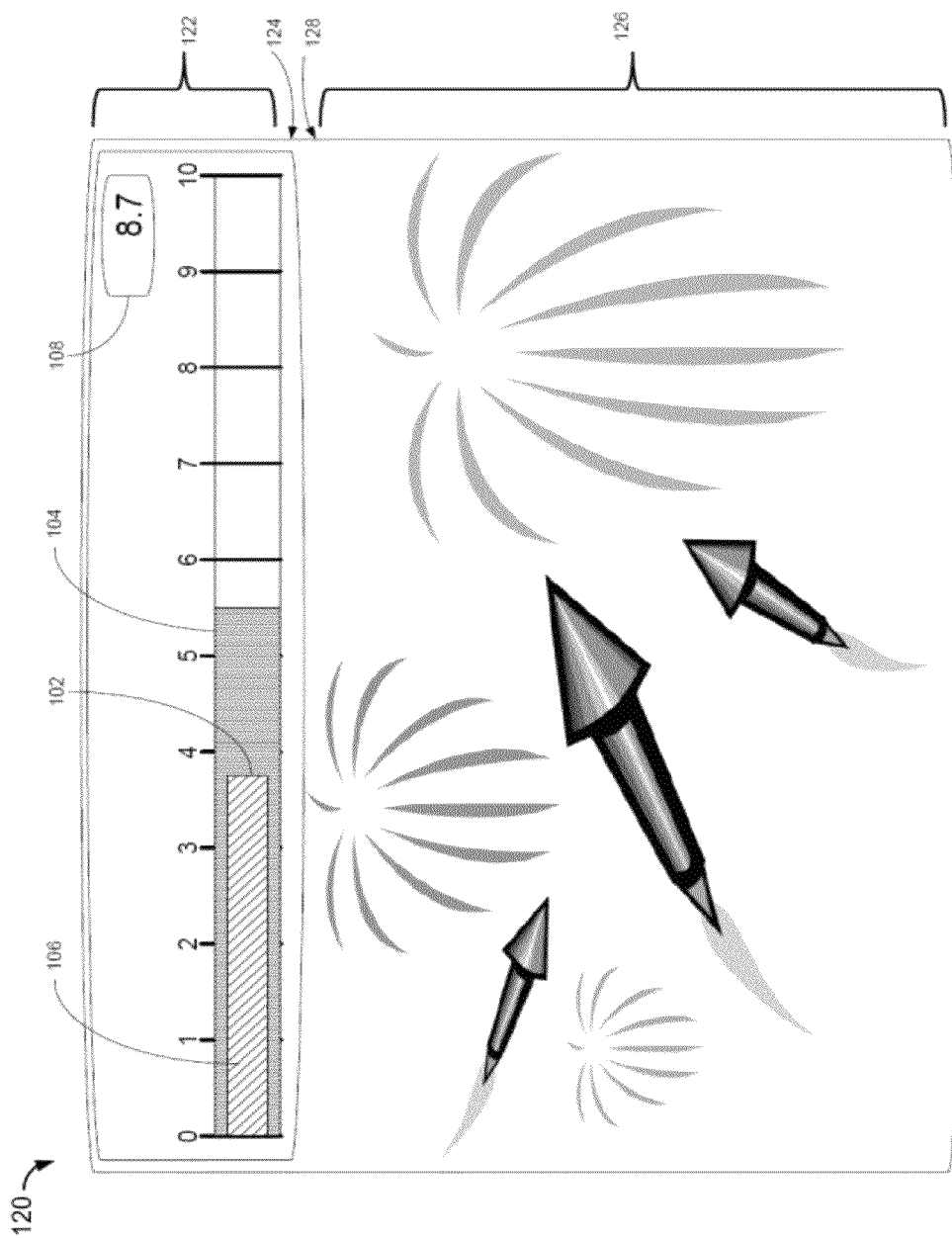
FIG. 11 is a front view of an aspect of an output or display of the feedback, e.g. in the form of an interactive gauge.
Figure 12:
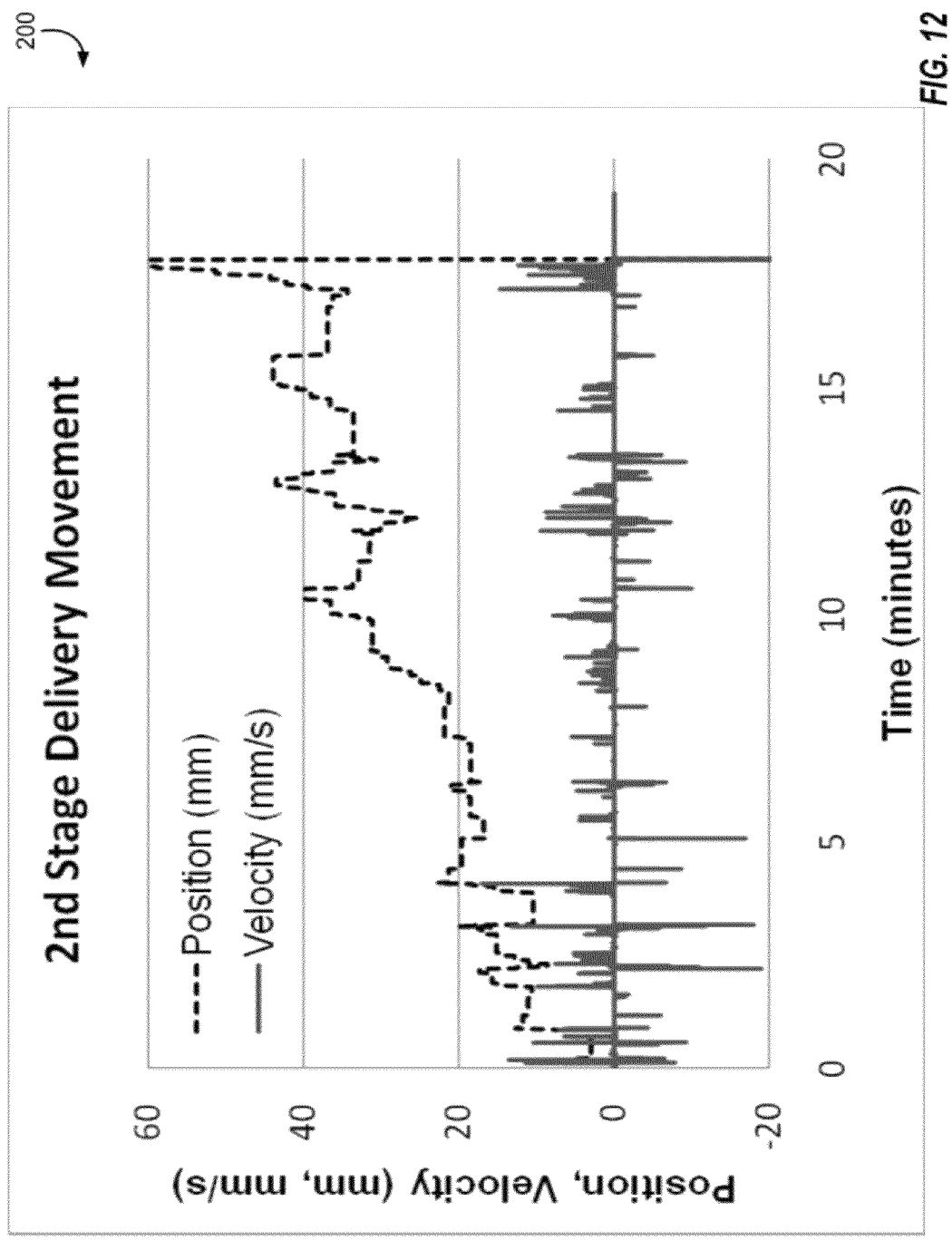
FIG. 12 is a graph of fetal position and velocity over time corresponding to fetal movement during a second stage of delivery.

Referring to FIGS. 9-12, in an aspect, user interfaces 100, 110 and 120 provide feedback 28 of the visual type in a variety of specific methods that can be selected by the mother. In these aspects, there may be at least three elements displayed to the mother: the movement of the baby during the current contraction or push 102, the target/goal distance of movement for the push 104, and the current velocity of the baby's movement 106. The feedback 28 may also include a display of the cumulative fetal movement 108. Referring to FIG. 12, the current movement 102, current velocity 106 and cumulative movement 108 may thus be a portion of, or a sum of the position or velocity of movement during the second stage of delivery 200.

Figure 9:
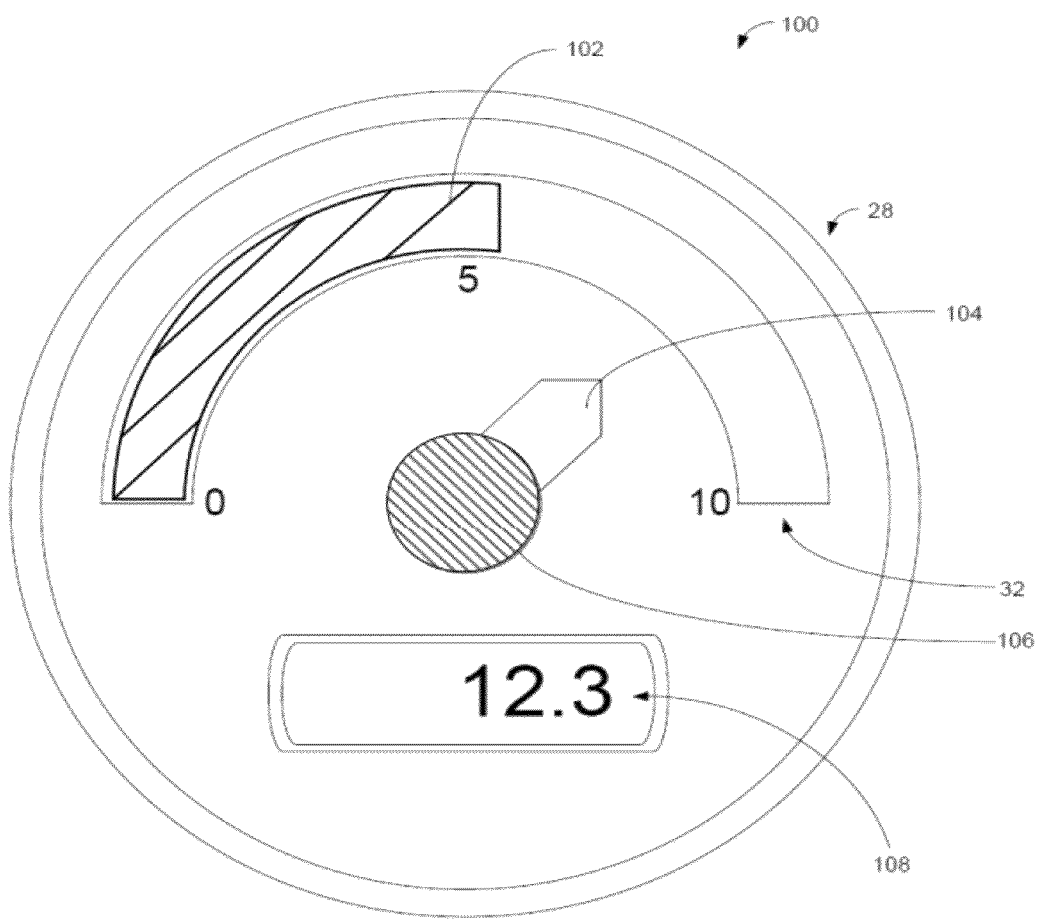
FIG. 9 is a front view of an aspect of an output or display of the feedback, e.g. in the form of a radial gauge.

The visual feedback can be provided in a more mechanical form such as a gauge, histogram or other relatively simple graphic such as the examples reflected in FIGS. 9 and 10. The feedback can also be more expansive and qualitative or game-like in nature such as a fireworks display as demonstrated in FIG. 11. In the latter example, the mother is rewarded for successful efforts when fetal movement causes population of the screen with objects of interest such as flowers or fireworks of increasing color, complexity, density and associations. In other words, such feedback 28 outputs may be referred to as a reward. Mothers can also be "rewarded" by other visual, audible or tactile tokens that are obtained when she produces fetal movement that meets certain goals thus, amplifying and encouraging her efforts. In this way the feedback both teaches the mother how to push and encourages maximal effectiveness.

Referring to FIG. 9, in one aspect, the feedback 28 (FIG. 1) may include a radial feedback gauge 100 displayed to the mother. The radial gauge 100 includes the distance measured for the current expulsive effort 102, for example, in millimeters. As needed the gauge maximum can scale to show the full amount of movement for the current pushing event. A dial indicator 104 is used to show a target value for the mother to strive to achieve for upcoming pushes. The center 106 of the gauge is an indicator, e.g. a changing color, to represent a current velocity of the baby. When velocity is less than a configurable value, 0.5 mm/s for instance, the indicator may be red. When over a certain configurable velocity value, 2 mm/s for instance, the indicator may be green. Further, for example, the indicator may be yellow when the current velocity is between the red maximum value and the green minimum value. A digital value gauge 108 is used to show cumulative movement for the duration of the second stage of labor. The starting point can be set to a negative value if desired to show progress towards and then beyond zero.

Referring to FIG. 10, in an aspect, the feedback 28 (FIG. 1) may be provided in the form of a linear feedback gauge 110 displayed to the mother. The linear gauge 110, in this example, includes three markers on a single scale. The marker 106 in the shape of a line is velocity in mm/s. The empty triangle 102 is movement in millimeters for the current pushing event and the filled triangle 104 is the distance target for the mother to strive to achieve. As with the radial gauge, the scale can be automatically adjusted to the appropriate level to show current values at a comprehendible resolution.

Referring to FIG. 11, user interface 120 include a linear gauge portion 122 for displaying a measured portion 124 of feedback 28 and a reward portion 126 for displaying a reward portion 128 of feedback 28 (FIG. 1). For example, measured portion 124 includes a bar 102 representing an amount of the current movement, lines 104 representing a movement target, an indicator 106 such as a color of bar 102 to represent a current velocity of the movement, and a numerical value 108 of the cumulative movement. Further, for example, reward portion 128 may include any visual representation pleasing to the mother to reward her for a good effort, such as fireworks, blooming flowers, or some aspect of a game that gets completed based on the expulsive efforts of the mother.

In an aspect, feedback 28 of the auditory type may be provided so that the mother can detect the fetal movement with or without the visual feedback. Examples of auditory feedback include simple tones with a given distance of movement or more complex sounds such as music of varied intensity or the sounds consistent with the visual theme such as the sound of exploding fireworks or popping budding or blooming flowers. The auditory feedback type may vary in pitch, volume or complexity relevant to the successful movement of the baby. The mother can select the auditory feedback type.

In an aspect, feedback 28 of the tactile type can also be relatively simple such as a vibration with the intensity or frequency modulated simply by the speed and distance of movement or in a more complex manner such as vibrations relating to the selected feedback theme.

In another aspect, stated more specifically, the described apparatus and methods include a mount affixed adjacent to the maternal pelvis or sacrum on one end and adjacent to the maternal introitus on the other end. The end near the introitus includes a support member that carries a guide wire to a sensor. The fixation of the mount to the maternal pelvis allows for precise detection of the movement of objects within the abdomen/pelvis, to which one end of the guide wire is attached, relative to the sensor while negating the movement of the objects within the abdomen and pelvis relative to other objects outside of the bony pelvis. These objects outside of the bones of the pelvis may include soft tissue, clothing, or any other object in the environment. Objects within the pelvis/abdomen whose movement may be measured based on the described aspects may include soft tissue, a baby, the uterus, the vagina, the bladder or any other abdominal/pelvic nerve, organ or vessel or any other device foreign to the body. Stated in another way, in an aspect, the fixation of mount to the pelvis maintains the constant position of the support member at, in or near the introitus relative to the bony pelvis, negating the effect of the movement of the pelvis and the object in the abdomen/pelvis relative to any other object outside of the pelvis. This configuration allows precise assessment of the movement of the object in the abdomen/pelvis relative to the pelvis despite movement of the pelvis in the environment.

Moreover, in an aspect, the described aspects may improve learning and motivation to a mother during labor based on these feedback methods, thereby providing the mother more control of the effort and hopefully decreasing the duration of labor and delivery.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. An apparatus for detecting movement of a fetus in a birth canal within a pelvic region of a body, comprising:
   a base affixable to a region adjacent the pelvic region such that the base is substantially stationary relative to the movement of the fetus;
   a projection member having a body extending between a first end and a second end, wherein the first end is attached to the base;
   a support member having a body and being positioned at the second end of the projection member;
   a flexible guide wire carried by the support member and having a first end configured to be attached to the fetus, a second end, and a fixed length, wherein the guide wire is movable between a first linear position within the birth canal of the body relative to the pelvic region and a second linear position within the birth canal of the body relative to the pelvic region, due to linear movement of the fetus in the birth canal relative to the pelvic region;
   a sensor adjacent to the guide wire and located a substantially fixed distance along a path of the guide wire from the support member, wherein the sensor is configured to detect movement of the guide wire between the first position and the second position; and a feedback unit having a processor and being in communication with the sensor, wherein the feedback unit is configured to generate feedback corresponding to the detected movement.

2. The apparatus of claim 1, wherein the support member is positionable to a location having a substantially fixed distance to the base.

3. The apparatus of claim 2, wherein the location is adjacent to the fetus.

4. The apparatus of claim 1, further comprising a guide tube carried by the support member, wherein the guide wire is movable at least partially within the guide tube.

5. The apparatus of claim 4, wherein the guide tube is connected to the sensor.

6. The apparatus of claim 1, wherein the feedback comprises visual feedback.

7. The apparatus of claim 1, wherein the feedback comprises audio feedback.

8. The apparatus of claim 1, wherein the feedback comprises tactile feedback.

9. The apparatus of claim 1, wherein the feedback changes relative to a characteristic of the movement of the guide wire between the first position and the second position.

10. The apparatus of claim 9, wherein the characteristic of the movement comprises at least one of a magnitude, a velocity, or an acceleration.

11. The apparatus of claim 1, wherein the feedback comprises a reward.

12. The apparatus of claim 1, wherein the feedback unit is further configured to generate a target.

13. The apparatus of claim 1, wherein the guide wire is movable in a sequence of movements between the first position and the second position, and wherein the feedback unit is further configured to generate a value representing a cumulative distance moved in at least a portion of the sequence of movements.

14. The apparatus of claim 1, wherein the guide wire is movable in a sequence of movements between the first position and the second position, wherein the sequence of movements corresponds to a movement of the fetus relative to a pelvic region of the body.

15. The apparatus of claim 1, wherein the guide wire is movable in a sequence of movements between the first position and the second position, wherein the sequence of movements corresponds to a fetal descent.

16. The apparatus of claim 1, further comprising a guide wire mount, the guide wire being connectable to the fetus via the mount.

17. The apparatus of claim 16, further comprising a fetal scalp electrode, wherein the guide wire mount removably connects the guide wire to the fetal scalp electrode.

18. The apparatus of claim 1, wherein the feedback unit is further configured to generate a value representing a distance moved from a starting point resulting from at least a portion of a sequence of movements, and wherein the projection member is configured to hold the support member in a position to receive the guide wire.

19. The apparatus of claim 1, wherein the guide wire is bendable relative to a longitudinal axis of the guide wire, and wherein the projection member is configured to hold the support member in a position to receive the guide wire.

20. The apparatus of claim 1, wherein the projection member comprises a substantially inelastic material sufficient to be moved and sufficient to hold the support member in a fixed position relative to the body and outside of the body.

21. The apparatus of claim 1, wherein the guide wire comprises a gauge or thickness sufficient to resist expanding or contracting during movement of the guide wire such that movement between the first position and the second position directly corresponds to the linear movement of the fetus within the birth canal.

* * * * *